US005732572A

United States Patent [19]
Litton

[11] Patent Number: 5,732,572
[45] Date of Patent: Mar. 31, 1998

[54] TEXTILE PROSTHESES HAVING PARTICULAR KNIT CONFIGURATION INCLUDING TWO-NEEDLE OVERLAP STITCH

[75] Inventor: Michael Litton, Ayrshire, Scotland

[73] Assignee: Vascutek Limited, Inchinnan, Scotland

[21] Appl. No.: 530,182

[22] PCT Filed: Mar. 15, 1994

[86] PCT No.: PCT/GB94/00511

§ 371 Date: Sep. 29, 1995

§ 102(e) Date: Sep. 29, 1995

[87] PCT Pub. No.: WO94/22394

PCT Pub. Date: Oct. 13, 1994

[30] Foreign Application Priority Data

Apr. 1, 1993 [GB] United Kingdom ............ 9306812

[51] Int. Cl.$^6$ ............................ A61F 2/06; D04B 1/22
[52] U.S. Cl. .......................... 66/195; 66/170; 623/1
[58] Field of Search .................... 66/190, 191, 192, 66/193, 194, 195; 623/1, 11, 12

[56] References Cited

U.S. PATENT DOCUMENTS

| | | | |
|---|---|---|---|
| 3,340,134 | 9/1967 | Porter et al. | 66/195 X |
| 3,474,644 | 10/1969 | Frank | 66/195 X |
| 4,015,451 | 4/1977 | Gajjar | 66/195 |
| 4,193,137 | 3/1980 | Heck | 66/195 X |
| 4,784,659 | 11/1988 | Fleckenstein et al. | 623/1 |
| 4,902,290 | 2/1990 | Fleckenstein et al. | 623/1 |
| 5,456,711 | 10/1995 | Hudson | 66/195 X |

FOREIGN PATENT DOCUMENTS

| | | |
|---|---|---|
| 0 237 037 | 9/1987 | European Pat. Off. |
| 2 194 406 | 3/1974 | France. |
| 31 29 350 | 2/1983 | Germany. |
| 602 093 | 7/1978 | Switzerland. |
| 1 383 722 | 2/1975 | United Kingdom. |
| 2 105 379 | 3/1983 | United Kingdom. |

OTHER PUBLICATIONS

M.W. King et al., "Designing Polyester Vascular Prostheses for the Future", *Medical Progress Through Technology*, vol. 9, 1983, pp. 217–226.

Primary Examiner—John J. Calvert
Attorney, Agent, or Firm—Sterne, Kessler, Goldstein & Fox P.L.L.C.

[57] ABSTRACT

The present invention relates to a fabric for the construction of knitted tubular grafts for use in cardiovascular surgery and to methods of manufacturing these grafts. The fabric of the present invention is constructed so that grafts formed from it will have an increased hoop modulus due to the fabric having a underlap of greater than two needle spaces in the bar nearer to the technical face of the fabric.

20 Claims, 6 Drawing Sheets

  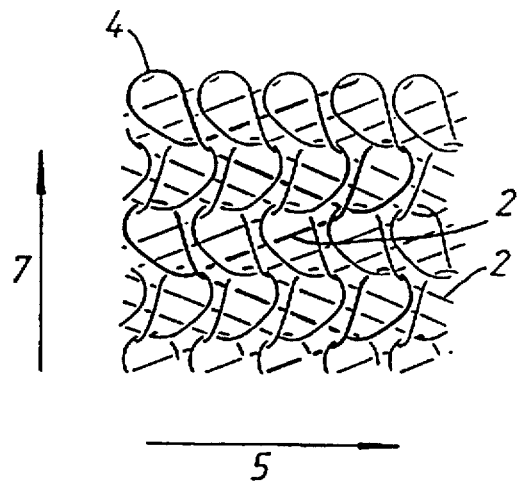
Fig.1a  Fig.1b
  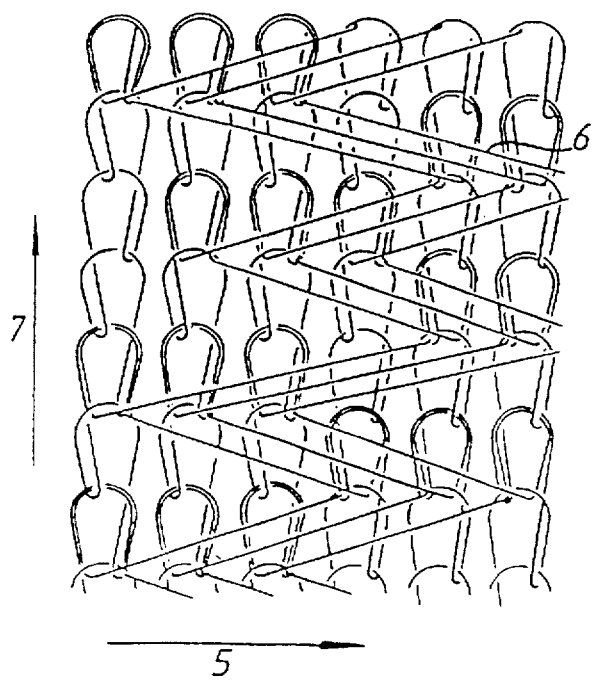
Fig.2a  Fig.2b

TEXTILE PROSTHESES HAVING PARTICULAR KNIT CONFIGURATION INCLUDING TWO-NEEDLE OVERLAP STITCH

The present invention relates to surgical prostheses and, in particular, to improved tubular grafts for use in cardiovascular surgery, to the fabric from which the grafts are constructed and to methods of manufacturing the fabric and the grafts.

For many years, tubular grafts have been used in cardiovascular surgery for the replacement and bypass of blood vessels. The tubular grafts used in such surgery are, in general, manufactured from woven or knitted textiles or from extruded polymers.

Vascular grafts are discussed in detail by King et al (*Med. Prog. Technol.*, 9, 217–226 (1983)) and this article contains a description of the ideal vascular graft which would, among other characteristics, be easily handled and sutured, would have similar elasticity, flexibility and compliance to the host vessel and would be sufficiently strong and durable to last for the life expectancy of the patient. The graft must have both longitudinal and radial strength and, in fact, a high hoop modulus (radial strength and resistance to dilatation) is particularly important since this ensures that the graft maintains its diameter and, hence, maintains the flow characteristics considered necessary by the surgeon. In addition, graft dilatation has been associated with false aneurysm at the suture site and widely dilated grafts have also the potential for thromboembolism.

Woven grafts may be either shuttle or rapier loom woven and are, in general, structurally stable, although some weaves do have a tendency to fray at the cut ends.

However, a serious disadvantage of most woven grafts is that they have poor compliance, limited elongation and limited water permeability. These properties, in combination, mean that many woven grafts are difficult to handle during implantation and suturing.

Alternatively, textile grafts may be knitted and the currently available knitted grafts fall into two main categories. Weft knitted structures have yarns which lie predominantly in the transverse direction and are relatively easy to construct. However, they do have the disadvantages that they are generally unstable and, although they have a good hoop strength, they have a low hoop modulus.

Warp knits such as the reverse locknit have yarns lying predominantly in the lengthwise direction and are more stable than weft knits, being less likely to unravel, and have good fray resistance characteristics. However, although stronger than weft knitted structures, they still have a tendency to dilate.

A third type of construction for vascular grafts is to form them from an extruded polymer such as expanded polytetrafluoroethylene (ePTFE).

ePTFE grafts differ from textile ones in that they are microporous rather than macroporous. This gives a device which is blood tight at implant but limits healing by tissue ingrowth. Bleeding from suture holes is a greater problem with ePTFE devices.

Because they are made by extrusion, it is difficult to make bifurcated devices from ePTFE. In contrast, textile bifurcates can be manufactured continuously without the eed for joins.

For several reasons, therefore, textile grafts are to be preferred to ePTFE ones although, as discussed above, they do have their own associated problems. It would be extremely advantageous to develop a new fabric for the constructions of grafts which has neither the stiffness of traditional woven materials, nor the low radial modulus of conventional knitted textiles.

In a first aspect of the present invention, there is provided a tubular knitted fabric for a surgical graft, characterised in that the fabric contains a Körper chain and is knitted using a stitch which has an underlap of greater than two needle spaces in the bar nearer to the technical face.

In the context of the present invention, the term "underlap" refers to the yarn between loops. Each underlap extends across the fabric and up one stitch. The loops themselves are referred to as the "overlaps".

In the context of the present invention, the term "bar" or "guide bar" refers to the device which determines the route of yarn sheets in the fabric.

In the context of the present invention, the term "technical face" refers to the side of the fabric on which loops are formed during the knitting process. The other side of the fabric is generally designated the "technical back".

Conventional knitted fabrics from which grafts are constructed are generally warp knitted using a stitch such as reverse locknit which is a 1×1 tricot on 2×1 tricot. A fabric of this construction has an underlap of two needle spaces in the bar nearer to the technical face and the fabrics of the present invention therefore have an underlap which is at least 50% longer than that of conventional fabrics.

The fabrics of the invention are superior in several respects to the fabrics which are currently available and, in particular, they are resistant to radial deformation (ie. they have a high hoop modulus).

One reason for the greater modulus of the fabrics of the present invention is that the long underlap means that the fabrics of the present invention contain fewer loops per unit length of yarn than conventional fabrics and they therefore have lower potential for radial expansion. In addition, and more importantly, when the fabric of the present invention is formed into a tube for use in a graft, the yarn of the underlap lies in a plane which is more nearly perpendicular to the longitudinal axis of the tube than is possible for the shorter underlaps of conventional fabrics. This is illustrated in FIGS. 1 to 4 and is made possible in the present invention because the underlap is so much longer than that of conventional fabrics. As discussed above, the underlap extends across the fabric and up one stitch and, therefore, it is quite clear that the longer the underlap, the nearer it will be to being perpendicular to the longitudinal axis of the tube. The fact that the underlap lies almost perpendicular to the longitudinal axis of the tube gives rise to an increased hoop modulus in the fabric of the present invention because the underlaps, in effect, form a band around the circumference of the tube.

A further advantage of the fabrics of the present invention is that they do not easily unravel and they have microstability, that is, all of the stitches are in a fixed position relative to one another. Thirdly, the fabric can be knitted on a standard knitting machine.

Another example of a suitable construction for the fabric of the present invention is a Köper or two-needle overlap chain knitted on a tricot, the tricot having an underlap of greater than two needle spaces. Tricot is of course a known stitch and Körper chains are also known. However, Köper chains are not known to have been used for any commercial application. One reason for this is that Köper chains are technically difficult to construct. In addition, in order to be commercially viable for most purposes, a fabric must be knitted at high speed. For example, a standard machine knits at speeds of about 2000 stitches per minute and speeds of up to 3000 stitches per minute have been achieved. However, because of the technicalities of the Köper chain, it can only be knitted at around 200 stitches per minute and this is much too slow for most uses.

Furthermore, a Köper chain knitted on a tricot is a new construction and is not known to have been used for any application. It is a difficult construction to manufacture but its very high radial modulus makes it extremely suitable for tubular grafts. Examples of constructions of this type which are suitable for use in the present invention are as follows:

Köper chain on 3×1 tricot;

Köper chain on 4×1 tricot;

Köper chain on 5×1 tricot;

In the constructions incorporating Köper chains, the size of the underlap in the bar nearer to the technical face is designated by the figures mentioned for the tricot part of the stitch, or when both parts are a tricot, by the second mentioned tricot structure. For example, for the chain on 3×1 tricot, the underlap in the bar nearer to the technical face is three needle spaces whereas, for the 1×1 tricot on 5×1 tricot it is five needle spaces.

All of these structures mentioned above have been found to be particularly suitable for the construction of vascular grafts because they have a better stability in all directions, particularly circumferentially, both on a micro and a macro scale than the stitches such as the reverse locknit which are generally used in conventional graft fabrics. However, the structures which incorporate the Köper chain are particularly preferred.

The fabric is usually constructed using a biocompatible yarn such as a polyester.

When the fabric is knitted using a stitch which has an underlap of three needle spaces in the bar nearer to the technical face, it is preferable that the yarn has a weight per unit length of from 30 to 100 decitex and more preferably from 35 to 60 decitex (one decitex is 1 g per 10 000 m). If the underlap is greater than three needle spaces, however, a finer yarn may be more suitable.

It is further preferred that the yarn is a multifilament yarn having, for example, a filament micron value of from 6 to 20 and preferably of from 10 to 15.

The yarn may be either flat or texturised although, if a chain on 3×1 tricot stitch is used, it is preferred that the yarn is texturised. For the yarn which forms a Köper chain this is less important and either type of yarn is equally preferred. In some cases, it may be advantageous to use a mix of flat and texturised yarn in the fabric construction.

In some cases, it may be useful to incorporate a marker into the fabric. One way in which the fabric may be marked is to knit it from yarn of a single colour except for a single yarn of a second colour which could be used as the marker.

The needles of the knitting machine should be of a gauge of at least 20/inch on each bed. However, it is preferred that the gauge is at least 28/inch and most preferably it will be 30/inch or greater on each bed.

The fabric density may be between 80 and 350 stitches per $cm^2$. Preferably, density may be between 160 and 220 stitches per $cm^2$.

In a second aspect of the invention, there is provided a process for the production of a fabric of the first aspect, the process comprising knitting a fabric from a suitable yarn using a stitch having an underlap of greater than two needle spaces in the bar nearer to the technical face.

It is preferred that the fabric is knitted as a tube so that it can be used as a graft without the need to sew a seam.

The fabric may be knitted on a machine in which there are at least 20 needles per inch on each bed although a preferred gauge is at least 28 or even 30 needles per inch. This ensures that the fabric is of a sufficiently fine gauge to be of use in a vascular graft.

The other preferred features of the method and the yarn are as described above for the fabric.

In a further aspect of the present invention, there is provided a tubular knitted surgical graft, characterised in that it is constructed from a fabric containing a Köper chain and which is knitted using a stitch which has an underlap of greater than two needle spaces in the bar nearer to the technical face.

It is preferred that the technical face of the fabric forms the outer face of the graft but this is certainly not essential for the functioning of the graft.

The tube may be bifurcated or straight (that is nonbifurcated) and will generally, though not invariably, be of circular cross section. The preferred yarns and gauge are as described above in relation to the fabric.

In a further aspect of the invention, there is provided a method for manufacturing a vascular graft as described above, the method comprising knitting a fabric in tubular form containing a Köper chain and using a stitch which has an underlap of greater than two needle spaces in the bar nearer to the technical face.

Again, it is preferred that the graft is knitted on a machine having at least 20 needles per inch, preferably 28/inch and more preferably 30/inch on each bed since this ensures that the fabric of the graft is of sufficiently fine gauge.

Once the tube has been knitted, corrugations may be formed in it and these may then be heat set in order to allow the tube to remain open rather than flat.

In addition, it is preferred that the tube is impregnated with a water soluble, physiologically acceptable material such as gelatin. The impregnation of the graft with such a material ensures that when the graft is first implanted it is impermeable so that the blood loss from the graft will not be unacceptably great. After implantation, the open structure of the knitted graft makes it possible for tissue to grow into it and, at the same time the gelatin, or other material, slowly dissolves.

At various stages of the production, the tube will be washed, cut into lengths and inspected for flaws. It is also usual to carry out physical tests of the fabric strength and permeability to ensure that these are within acceptable limits. In general, the grafts will, of course be packaged in sterile packaging, sterilised, desiccated and enclosed in the final outer packaging. It is also usual to test the grafts to check that they are of acceptable sterility and pyrogenicity.

The invention will now be further described in the following examples and with reference to the accompanying drawings in which:

FIG. 1a is a diagrammatic representation of a chain;

FIG. 1b is a diagrammatic representation of a 3×1 tricot which can be superimposed on the chain of FIG. 1a to give a Delaware structure suitable for use in the present invention;

FIG. 2a is a diagrammatic representation of a chain;

FIG. 2b is a diagrammatic representation of a mixed 3×1, 4×1 tricot which can be superimposed on the chain of FIG. 2a to give a Delaware structure suitable for use in the present invention;

FIGS. 1 to 3 illustrate the types of stitch which are useful in the present invention and FIG. 4 illustrates the reverse locknit construction which is often used for the construction of conventional grafts.

FIG. 1a illustrates the chain stitch used in the bar further from the technical face and FIG. 1b shows a 3×1 tricot which, in the fabrics of the present invention, is in the bar nearer to the technical face. The figure shows the underlaps 2 and the loops 4 and it can be seen that each underlap passes from one row to the row above or below and also crosses two loops (that is three needle spaces).

FIG. 2 illustrates an alternative construction. FIG. 2a again illustrates a chain which is in the bar further from the technical face but in the bar nearer to the technical face a mixed 3×1, 4×1 tricot is used. However, it can easily be seen that the underlaps 6 in the mixed tricot pass from one vertical row to the adjacent one and, that some of them cross three and some four needle spaces.

Figure 3A:
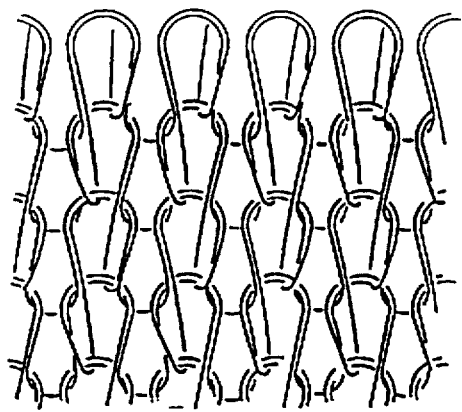
FIG. 3a is a diagrammatic representation of a Köper chain.
Figure 3B:
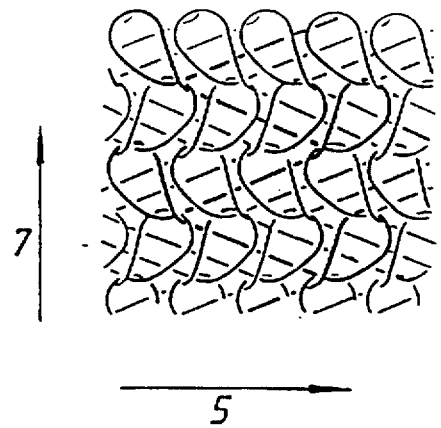
FIG. 3b is a diagrammatic representation of a 3×1 tricot which can be superimposed on the Köper chain of FIG. 3a to give a structure suitable for use in the present invention.

FIG. 3 shows another stitch useful in the present invention. This time, there is a Köper chain in the bar further from the technical face (FIG. 3a) and a 3×1 tricot in the bar nearer to the technical face (FIG. 3b). The bar nearer to the technical face is therefore identical to that shown in FIG. 1b.

Figure 4A:
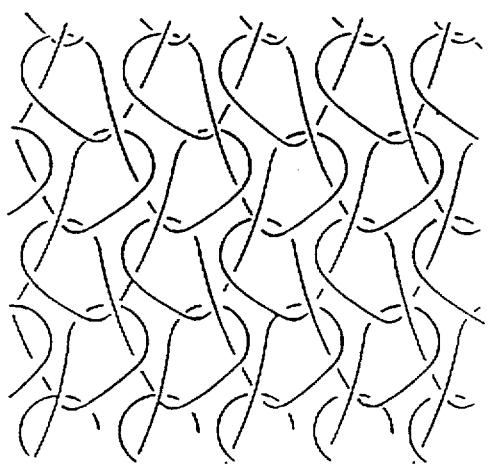
FIG. 4a is a diagrammatic representation of a 1×1 tricot.
Figure 4B:
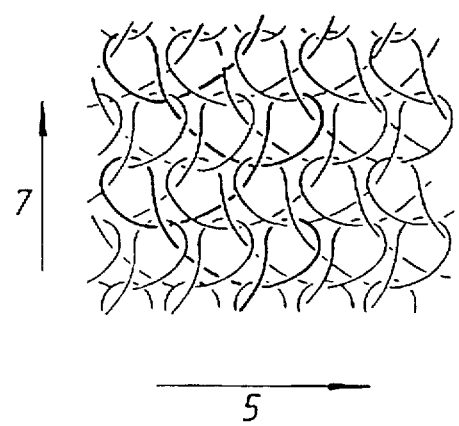
FIG. 4b is a diagrammatic representation of a 2×1 tricot which can be superimposed on the structure of FIG. 4a to give the reverse locknit commonly used in prior art fabrics.

Finally, FIG. 4 illustrates a reverse locknit of the type commonly used in grafts of conventional construction. This time, there is a 1×1 tricot in the bar further from the technical face and this is shown in FIG. 4a. In the bar nearer to the technical face, a 2×1 tricot is used and this is illustrated in FIG. 4b. From this figure it can be seen that each of the underlaps 8 crosses only one loop (two needle spaces) in passing from one vertical row to the next.

Clearly, therefore, the main difference between conventional constructions and those of the present invention is that in the fabrics of the present invention, the underlaps in the bar nearer to the technical face cross a greater horizontal distance each time they pass from one row to the next than is the case with the conventional fabrics (by horizontal, is meant the direction marked by arrow 5 on FIGS. 1 to 4; vertical is shown by arrow 7). This means that the angle between rows of loops and the underlap is much smaller in the fabrics of the invention than in conventional fabrics and this is illustrated in the figures. If the fabric is in a tubular form with the rows of loops in the horizontal direction marked by arrow 5 passing around the circumference of the tube, then the underlaps will pass around the tube and effectively hold together the vertical columns of loops which run in a direction parallel to arrows 7. The longer the underlap and the closer it lies to the horizontal, the greater will be its effect and it is this effect which is responsible for the greatly increased radial modulus of the fabrics of the present invention.

EXAMPLE 1

Knitting of Fabric

Straight (non-bifurcated) tubular vascular grafts were knitted on a 16 bar double bed double drum raschel frame of gauge 30/inch on each bed. The yarn on bars 8 and 9 is 1.44.27 (ie single yarn, 44 decitex, 27 filaments) T56 texturised DACRON™ and the yarn on the other bars was 2.44.27 texturised DACRON™. The details of the knitting process are shown in FIG. 5 which illustrates the details of the Köper stitch which was used to construct the fabric at a density of 210 stitches per $cm^2$.

Figure 5:
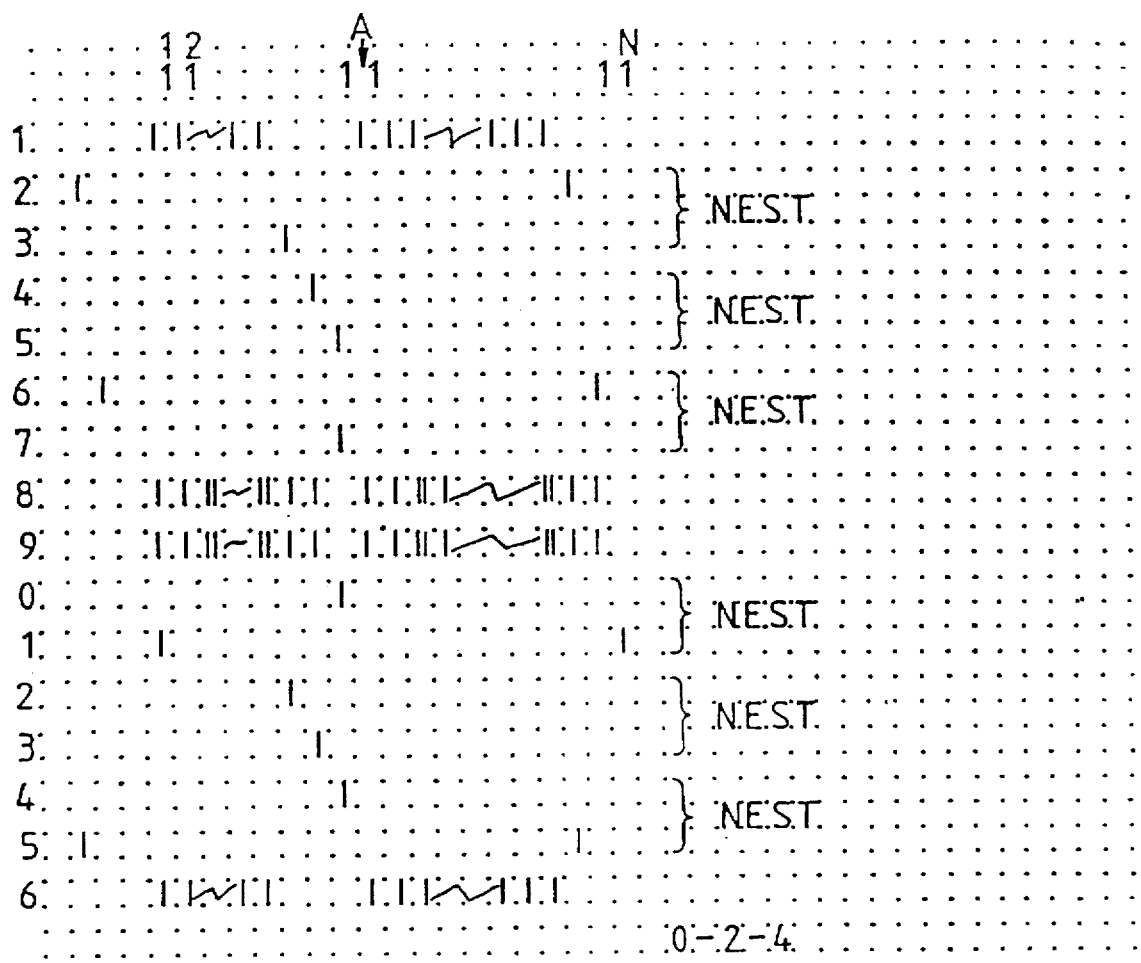
FIG. 5 is a pin diagram which gives technical information for the knitting of a fabric according to the present invention.

The full details of the pattern chain, which accompany the pin diagram of FIG. 5, are as follows:

| Bar | Body | | | | Legs | | | |
|---|---|---|---|---|---|---|---|---|
| 1 | 2-0 | 4-4 | 6-8 | 4-4 | As body | | | |
| 2 | 2-0 | 6-8 | 10-12 | 6-4 | As body | | | |
| 3 | As one | | | | 2-0 | 6-6 | 6-6 | 6-4 |
| 4 | As one | | | | 2-0 | 2-2 | 4-4 | 2-0 |
| 5 | As one | | | | 2-2 | 2-4 | 6-8 | 2-2 |
| 6 | 2-0 | 6-8 | 6-8 | 2-0 | As body | | | |
| 7 | As eight | | | | 4-2 | 2-4 | 2-4 | 4-2 |
| 8 | 4-0 | 2-2 | 0-4 | 2-2 | 4-0 | 2-2 | 0-4 | 2-2 |
| 9 | 2-2 | 0-4 | 2-2 | 4-0 | As body | | | |
| 10 | As nine | | | | 2-0 | 0-2 | 0-2 | 2-0 |
| 11 | 2-0 | 0-2 | 0-2 | 2-0 | As body | | | |
| 12 | As sixteen | | | | 6-4 | 6-6 | 6-6 | 2-0 |
| 13 | As sixteen | | | | 6-6 | 6-8 | 6-8 | 4-4 |
| 14 | As sixteen | | | | 2-2 | 6-8 | 2-4 | 2-2 |
| 15 | 6-4 | 10-12 | 6-8 | 2-0 | As body | | | |
| 16 | 4-4 | 6-8 | 4-4 | 2-0 | As body | | | |

EXAMPLE 2

One potential problem of vascular prostheses is dilatation. This is a progressive increase in diameter with time and is most often seen with knitted grafts. The mechanism of dilatation is not clear but involves a rearrangement of the textile structure. It is difficult to model this accurately in vitro but an indication of the tendency of a graft to dilate can be gained from studying the relationship of diameter and pressure.

Measurement of Diameter/Pressure Relationship

Figure 8:
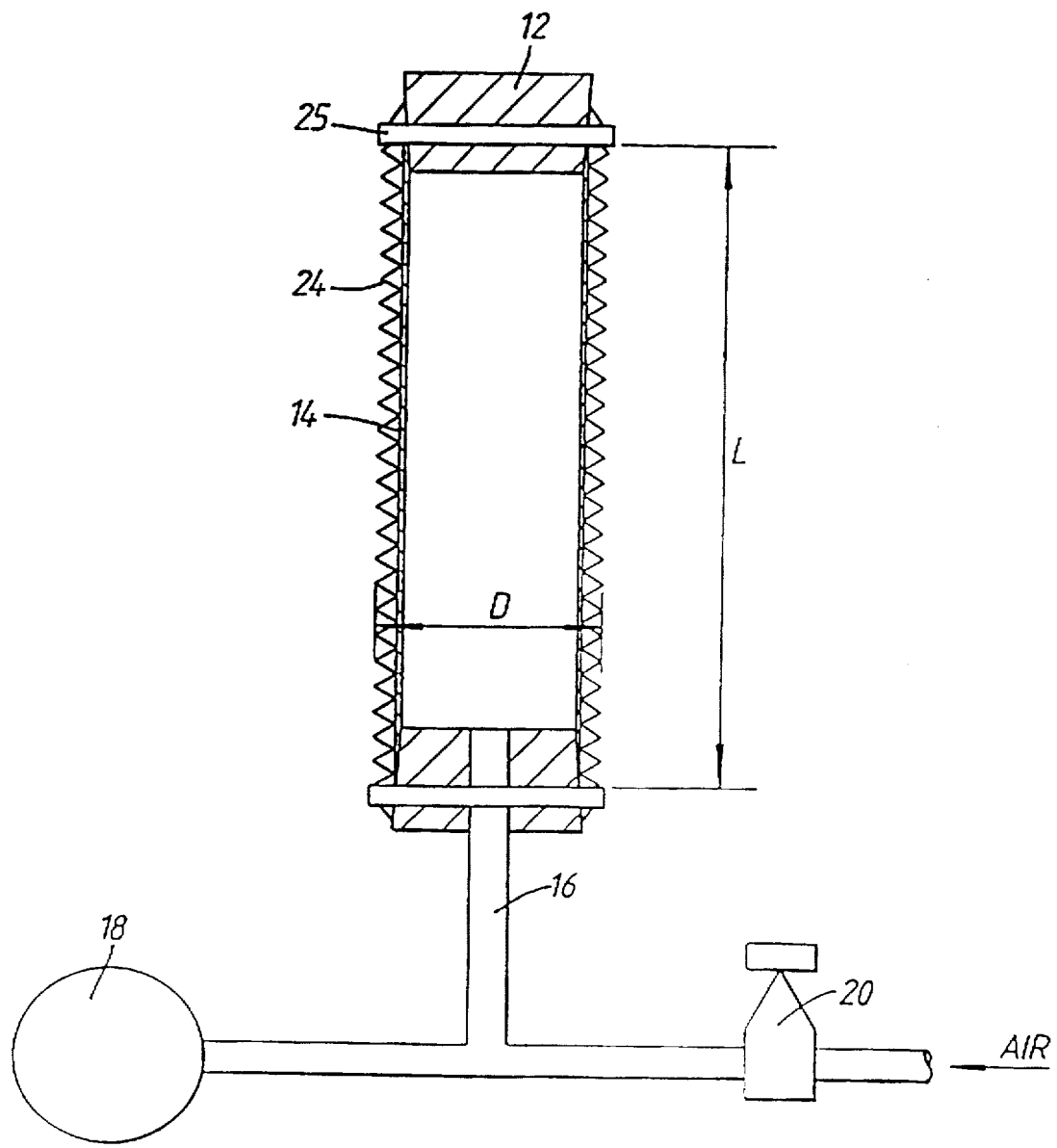
FIG. 8 is a diagram of the apparatus used to measure the relationship between graft diameter and pressure.

The measurement of the variation of diameter with increasing pressure of various grafts was carried out on the apparatus shown in FIG. 8. The apparatus shown in the Figure comprises a stand (not shown) on which is mounted a plug 12 from which a latex liner 14 is suspended. The lower end of the latex liner 14 is sealed and protruding into the sealed end is a tube 16 through which air can pass into the liner 14. Connected to the tube 16 is a pressure gauge 18 and a regulator 20 to regulate the flow of air through the tube 16. Mounted adjacent the latex liner 14 in such a way that it spans the diameter of the liner is a gauge (not shown) for measuring the diameter D of the graft.

In order to measure the variation in diameter of a graft with increasing pressure, a graft 24 is mounted around the latex liner using a clamp 25 so that the inner surface of the graft 24 is in contact with the outer surface of the liner 14. The gauge will then span the diameter of the graft so that the diameter of the graft can be measured.

Air is then passed through the tube 16 into the liner 14 so that the liner becomes pressurised and thus exerts a pressure on the graft 24. The diameter of the graft 24 is then measured at various different pressures.

If desired, the graft length L can also be recorded and the variation in diameter with pressure measured for different lengths of graft.

Results

Figure 6:
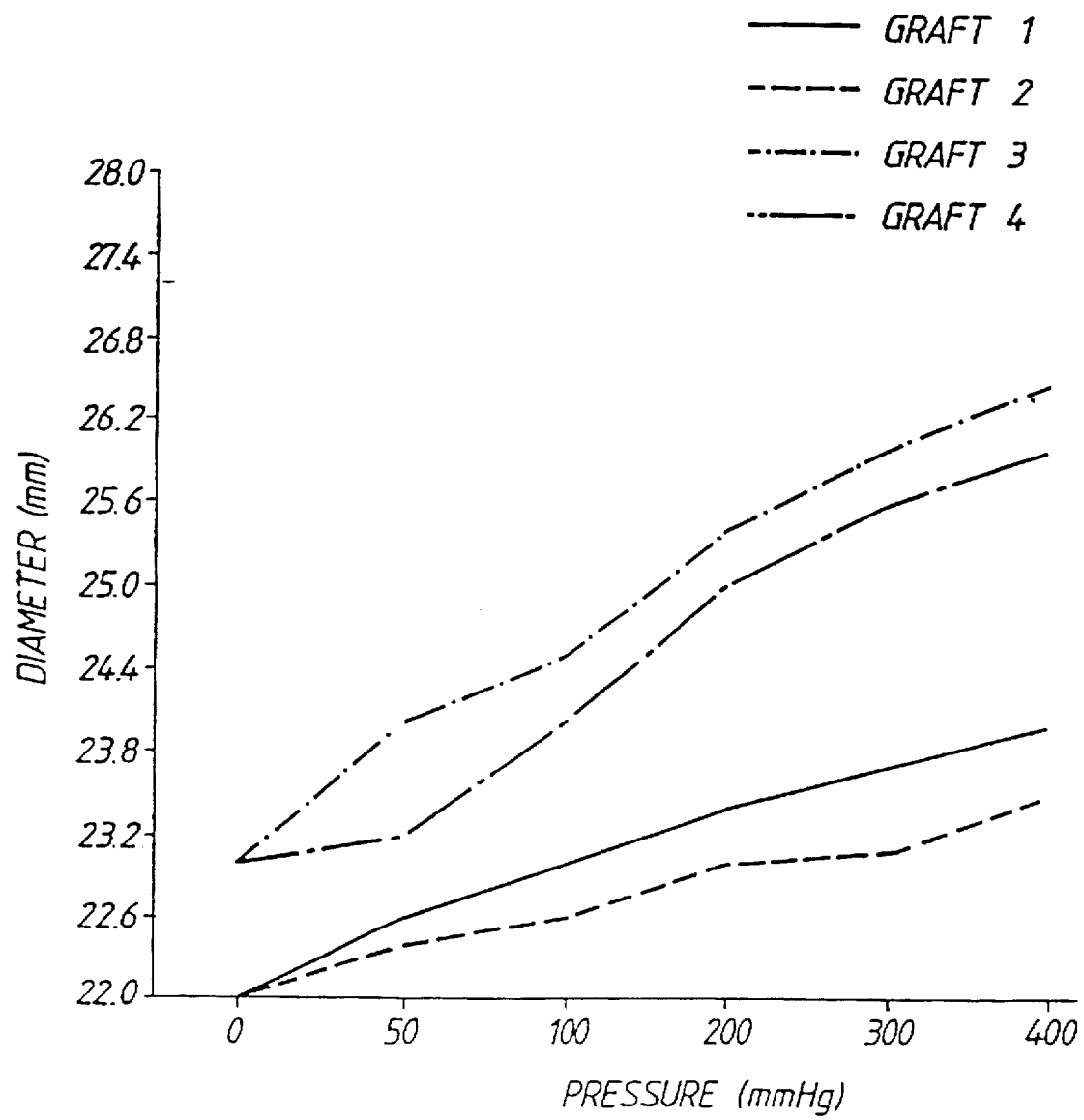
FIG. 6 is a plot of the variation of graft diameter with pressure for various grafts of the present invention.

Table 1 and FIG. 6 both show the effect of pressure on the diameters of four vascular grafts constructed from a fabric according to the present invention.

Graft 1 was a graft knitted according to Example 1, washed at a temperature of 90° C. and then sealed with gelatin.

Graft 2 was a graft knitted according to Example 1, washed at a temperature of 40° C. and then sealed with gelatin.

Graft 3 was a graft knitted according to Example 1 then washed at a temperature of 90° C.

Graft 4 was a graft knitted according to Example 1 then washed at a temperature of 40° C.

TABLE 1

| 1. | | 2. | | 3. | | 4. | |
|---|---|---|---|---|---|---|---|
| Pressure mmHg | Diameter mm | Pressure mmHg | Diameter mm | Pressure mmHg | Diameter mm | Pressure mmHg | Diameter mm |
| 0 | 22 | 0 | 22 | 0 | 23 | 0 | 23 |
| 50 | 22.6 | 50 | 22.4 | 50 | 24 | 50 | 23.2 |
| 100 | 23 | 100 | 22.6 | 100 | 24.5 | 100 | 24 |
| 200 | 23.4 | 200 | 23 | 200 | 25.4 | 200 | 25 |
| 300 | 23.7 | 300 | 23.1 | 300 | 26 | 300 | 25.6 |
| 400 | 24 | 400 | 23.5 | 400 | 26.5 | 400 | 26 |

From Table 1 and FIG. 6, it can be seen that none of the grafts used expanded greatly in diameter even at a pressure of 400 mm Hg.

Figure 7:
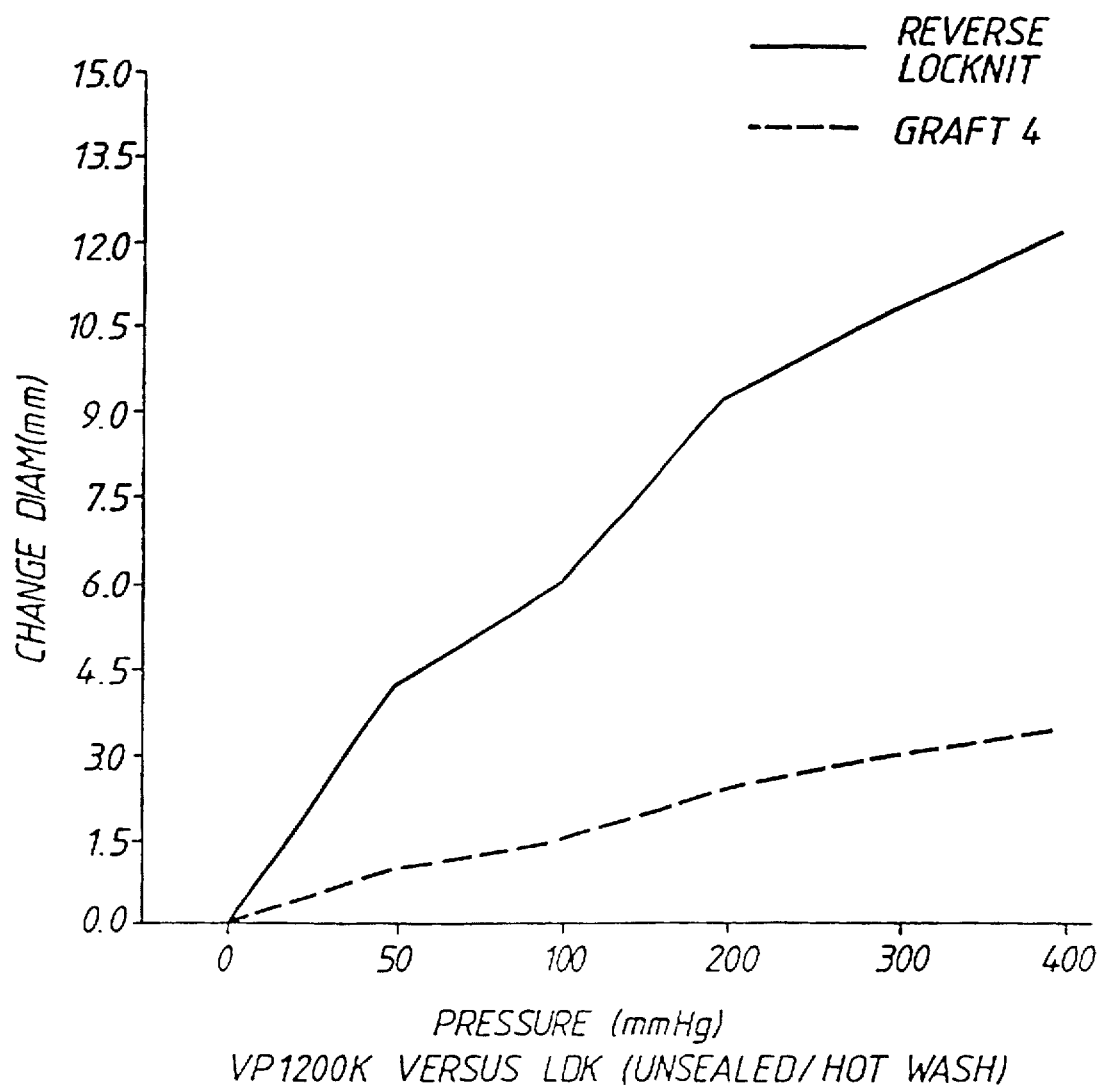
FIG. 7 is a plot of the variation of graft diameter with pressure which compares a graft of the present invention with a graft knitted using prior art methods.

Tables 2 and 3 and FIG. 7 demonstrate that using the fabric of the present invention it is possible to form grafts having much greater radial strength than grafts formed from fabrics of conventional construction.

Table 2 shows variation with pressure of the diameter and the change in diameter of a vascular graft knitted using the same yarn but in a reverse locknit construction and Table 3 shows similar results for Graft 3 above which was the weakest of the grafts of the present invention.

TABLE 2

| Pressure (mmHg) | Diameter (mm) | Δ Diameter (mm) |
|---|---|---|
| 0 | 24 | 0 |
| 50 | 28.2 | 4.2 |
| 100 | 30 | 6 |
| 200 | 33.3 | 9.3 |
| 300 | 34.9 | 10.9 |
| 400 | 36.3 | 12.3 |

TABLE 3

| Pressure (mmHg) | Diameter (mm) | Δ Diameter (mm) |
|---|---|---|
| 0 | 23 | 0 |
| 50 | 24 | 1 |
| 100 | 24.5 | 1.5 |
| 200 | 25.4 | 2.4 |
| 300 | 26 | 3 |
| 400 | 26.5 | 3.5 |

FIG. 7 is a plot showing a direct comparison of the data presented in Tables 2 and 3.

From a comparison of the Tables 2 and 3 and a study of FIG. 7, it can be seen that the diameter of the graft of the present invention varied by a much smaller amount than the conventionally constructed graft. In addition, it should be borne in mind that the graft on which these comparative experiments were carried out was the one which performed the least well of the grafts of the present invention.

It can therefore be seen that the fabric of the present invention represents a considerable improvement over prior art knitted fabrics generally used for surgical grafts since it has a much higher radial modulus.

I claim:

1. A tubular knitted fabric for a surgical graft, the fabric being defined by a technical face and a technical back, wherein, during knitting of the fabric, the route of yarn sheets in the fabric is determined by bars, and wherein the fabric contains a two-needle overlap chain and is knitted using a stitch which has an underlap of greater than two needle spaces in the bar nearer to the technical face.

2. A knitted fabric as in claim 1 which has one of the following constructions:

two-needle overlap chain on 3×1 tricot;

two-needle overlap chain on 4×1 tricot;

two-needle overlap chain on 5×1 tricot.

3. A knitted fabric as claimed in claim 1 which is constructed from a polyester yarn.

4. A knitted fabric as claimed in claim 1 which is constructed from yarns having a weight per unit length of from 30 to 100 decitex.

5. A knitted fabric as claimed in claim 4, wherein the yarn has a weight per unit length of from 35 to 60 decitex.

6. A knitted fabric as claimed in claim 1 constructed from a multifilament yarn.

7. A knitted fabric as claimed in claim 6, wherein the yarn has a filament micron value of from 6 to 20.

8. A knitted fabric as claimed in claim 1 constructed from a flat yarn.

9. A knitted fabric as claimed in claim 1 constructed from a texturized yarn.

10. A knitted fabric as claimed in claim 1 constructed from a mix of texturized and flat yarns.

11. A knitted fabric as claimed in claim 1 comprising a marker.

12. A knitted fabric as claimed in claim 11, wherein the marker comprises a yarn of a different color from the rest of the fabric.

13. A process for the production of a fabric, the process comprising the steps of:

knitting a fabric in tubular form, said fabric defined by a technical face and a technical back;

determining the route of yarn sheets in the fabric using bars; and using a stitch comprising a two-needle overlap chain and having an underlap of greater than two needle spaces in the bar nearer to the technical face.

14. A process as claimed in claim 13, in which the fabric is knitted as a straight tube.

15. A process as claimed in claim 13, in which the fabric is knitted as a bifurcated tube.

16. A process as claimed in claim 13, wherein the fabric is knitted on a machine having at least 20 needles per inch.

17. A process as claimed in claim 13, further comprising the step of forming corrugations in the tube.

18. A process as claimed in claim 13, further comprising the step of impregnating the tube with a water soluble physiologically acceptable material such as gelatin.

19. A tubular surgical graft knitted from a fabric defined by a technical face and a technical back, wherein, during knitting of the fabric, the route of yarn sheets in the fabric is determined by bars, and wherein the fabric contains a two-needle overlap chain and is knitted using a stitch which has an underlap of greater than two needle spaces in the bar nearer to the technical face.

20. A knitted surgical graft as claimed in claim 19 which is a bifurcated tube.

* * * * *